United States Patent [19]

Shelley

[11] Patent Number: 4,997,447
[45] Date of Patent: Mar. 5, 1991

[54] SCREW-THREADED ACETABULAR COMPONENT OF HIP JOINT PROSTHESIS

[75] Inventor: Philip Shelley, St. Paul, Minn.

[73] Assignee: Minnesota Mining and Manufacturing Company, St. Paul, Minn.

[21] Appl. No.: 394,755

[22] Filed: Aug. 16, 1989

[51] Int. Cl.$^5$ .............................................. A61F 2/34
[52] U.S. Cl. ................................................... 623/22
[58] Field of Search ...................... 623/16, 18, 19, 20, 623/22, 23

[56] References Cited

U.S. PATENT DOCUMENTS

| 3,894,297 | 7/1975 | Mittelmeier et al. | 3/1 |
| 4,563,778 | 1/1986 | Roche et al. | 623/22 |
| 4,596,580 | 6/1986 | Weill | 623/22 |
| 4,632,111 | 12/1986 | Roche | 128/303 |
| 4,650,491 | 3/1987 | Parchinski | 623/22 |
| 4,662,891 | 5/1987 | Noiles | 623/22 |
| 4,715,859 | 12/1987 | Schelhas et al. | 623/22 |
| 4,795,469 | 1/1989 | Oh | 623/22 |

FOREIGN PATENT DOCUMENTS

| 0065482 | 11/1982 | European Pat. Off. . |
| 0142759 | 5/1985 | European Pat. Off. . |
| 0190083 | 1/1986 | European Pat. Off. . |
| 0179736 | 4/1986 | European Pat. Off. . |
| 2950536 | 12/1979 | Fed. Rep. of Germany . |
| 8810783 | 8/1988 | Fed. Rep. of Germany . |
| WO87/05490 | 3/1987 | PCT Int'l Appl. . |
| 2080118 | 2/1982 | United Kingdom . |

OTHER PUBLICATIONS

Socket Fixation Using a Metal-Backed Acetabular Component for Total Hip Replacement; The Journal of Bone and Joint Surgery, vol. 64A, pp. 745-748.
Stress Distribution in the Acetabular Region I. Before and After Total Joint Replacement; 15 J. Biomechanics 155-164, (Pergamon Press Ltd. 1982).
Stress Distribution in the Acetabular Region II. Effects of Cement Thickness and Metal Backing of the Total Hip Acetabular Component, 15 J. Biomechanis, 165-170, (Pergamon Press 1982).
Advances in Total Hip Replacement by W. Harris.
Mecron Med. Produkte GmbH, advertisement: "MECRING TM".

Primary Examiner—David J. Isabella
Attorney, Agent, or Firm—Donald M. Sell; Walter N. Kirn; Stephen W. Bauer

[57] ABSTRACT

An acetabular implant of a hip joint prosthesis comprising a metal cup shell (2) having an external self-tapping thread extending around the circumference of the shell. The thread is divided into a plurality of segments (8, 10) by a plurality of tapping grooves (16). The thread radius (Ra, Rb, Rc, Rd) of the thread segments (8, 10) progressively decreases from the leading end (12) to the trailing end (14) of a segment (8 or 10). The tapping grooves (16) are preferably arranged in pairs dividing the thread into alternating long (8) and short (10) segments. The construction of the thread reduces the propensity of the implant to jam during insertion.

16 Claims, 2 Drawing Sheets

SCREW-THREADED ACETABULAR COMPONENT OF HIP JOINT PROSTHESIS

FIELD OF THE INVENTION

This invention relates to a hip joint prosthesis and in particular to the acetabular component of a hip joint prosthesis having a screw-thread for anchorage within the acetabulum.

BACKGROUND OF THE INVENTION

Prosthesis for the replacement of hip joints are well known. Originally, only the ball-end on the head of the femur could be replaced but it has since proved possible to replace either part of the hip joint, i.e., the acetabular socket of the joint or the ball-end on the femur.

Known acetabular cup implants, which form the socket portion of an artificial hip joint, comprise a metal cup shell, which is secured within the acetabulum in the pelvic bone of a patient, and an inner liner of plastic material that provides a spherical bearing surface for receiving the ball portion of the joint. The metal cup shell may be provided with an external thread to facilitate anchorage to the pelvic bone or may be secured by other means such as cement or screws.

Metal cup shells having an external screw thread are widely used and are disclosed, for example, in U.S. Pat. Nos. 3,894,297 and 4,662,891 and International Publication No. WO 87/05490. However it is often difficult to fully insert metal cup shells having self tapping screw threads, as is necessary to ensure contact of the entire surface area of the outside of the metal cup with the surface of the acetabulum to provide maximum transfer of forces from the prosthesis to the pelvic bone. The implants often have a tendency to jam, and great force is necessary to rotate the implant in either direction, which may cause bone fracture.

SUMMARY OF THE INVENTION

An acetabular component of a hip joint prosthesis is now provided that reduces the propensity of the implant to jam during insertion.

Generally, an acetabular implant of the invention comprises a metal cup shell having an external self-tapping thread extending around the circumference of the shell. The thread is divided into a plurality of segments by a plurality tapping grooves. The thread radius of the thread segments progressively decreases from the leading end to the trailing end of a segment.

Other features will be pointed out hereinafter.

BRIEF DESCRIPTION OF THE DRAWINGS

The invention will now be described with reference to the accompanying drawings in which.

Corresponding reference characters indicate corresponding parts throughout the several views of the drawings.

DETAILED DESCRIPTION OF PREFERRED EMBODIMENTS

Figure 1:
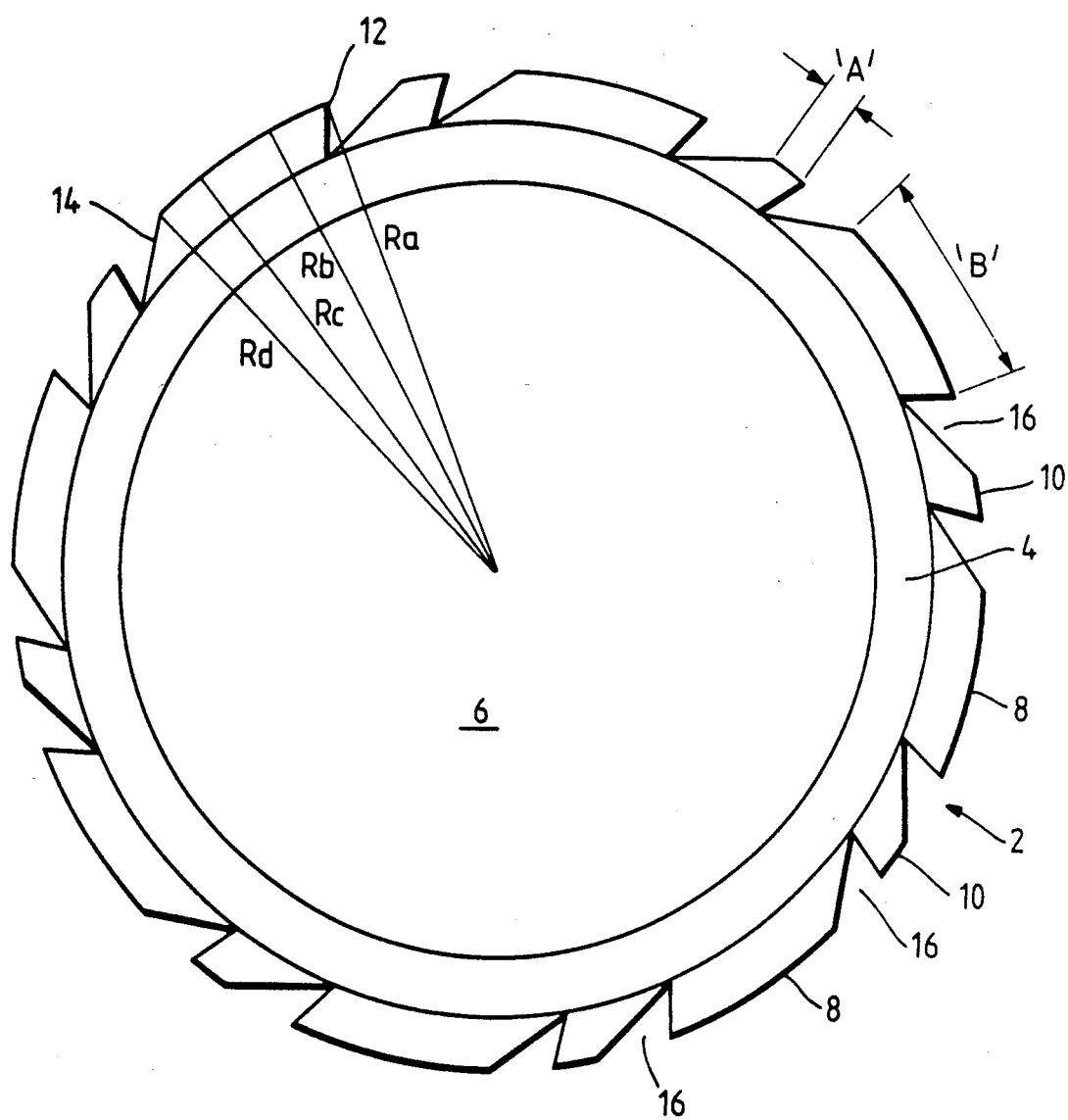
FIG. 1 is a plan view of a metal cup shell in accordance with the invention.
Figure 2:
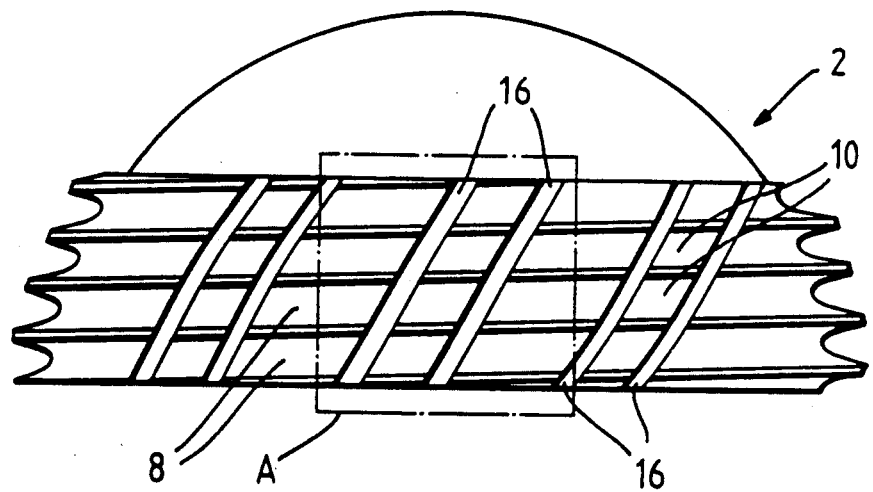
FIG. 2 is a side elevation of the metal cup shell of FIG. 1.
Figure 3:
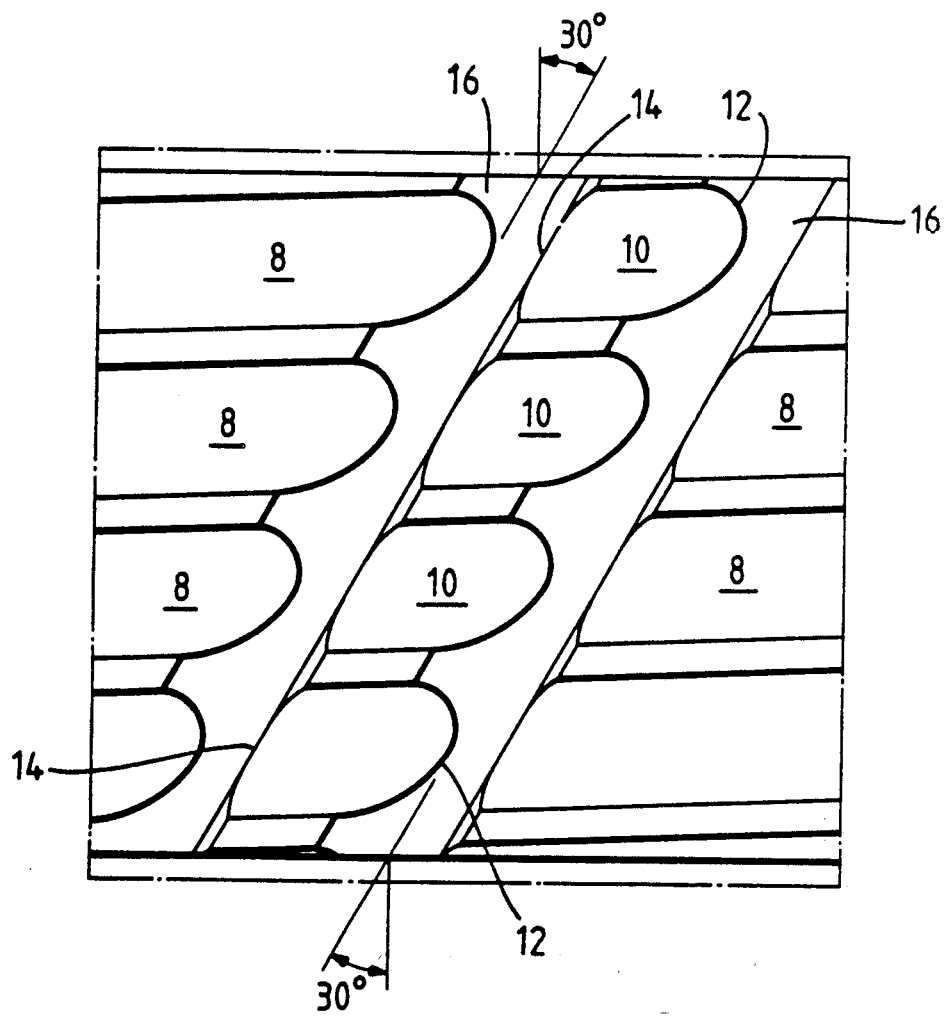
FIG. 3 is an enlarged view of section A in FIG. 2.

The metal cup shell 2 may be fabricated from any suitable metal, e.g., titanium or an alloy of titanium with aluminum and/or vanadium. The cup shell 2 comprises a wall 4 which may be generally hemispherical or frusto-conical defining a hemispherical cavity 6. A plastic liner (not shown) is inserted into the cavity 6 to define the spherical bearing surface for the ball portion of the hip joint.

The metal cup shell 2 is provided along its outer surface with a self-tapping thread comprising alternating long thread segments 8 and short thread segments 10. The length 'B' of the long segments 8 is preferably between 1.5A and 18A, where 'A' is the length of the short segments 10.

Each thread segment 8 or 10 has a thread radius (as measured from the outside of the thread segment to the longitudinal axis of the metal cup shell 2) which progressively decreases from the leading end 12 to the trailing end 14 of the segment 8 or 10. This is believed to reduce implant jamming upon insertion due to the visco-elasticity of bone, which otherwise deflects away from the cutting edges on thread segments and consequently binds upon the trailing portion of the thread segments. The decrease is preferably at least 3% of the thread depth more preferably 10% and generally not more than 30%. This arrangement also ensures the leading end 12 of a thread segment 8 or 10 presents a sharp cutting face towards the bone thereby cutting the bone rather then deflecting the bone. Thus in the drawing:

$Ra > Rb > Rc > Rd$.

The width of each thread segment 8 and 10 preferably decreases from the leading end 12 to the trailing end 14 thereby further reducing the tendency of bone to bind on the trailing portion 14 of a thread segment 8 or 10.

The short and long thread segments 8 and 10 are separated by tapping grooves 16, with the total volume of the tapping grooves preferably exceeding the total volume of all of the thread segments. The tapping grooves 16 are inclined at an angle of 30° with respect to the axis of the cup shell.

The purpose of the tapping grooves 16 is to provide a space for the bone fragments cut by the thread segments 8 or 10. Thus it is important that the total volume of the tapping grooves 16 is at least equal to the volume of bone debris generated in the self-tapping process; otherwise, the tapping grooves 16 become blocked with compact bone debris, and further insertion of the implant 2 is prevented. Inadequate provision of tapping grooves 16 may even lead to jamming of the implant 2. The total volume of the tapping grooves 16 of the implant 2 is preferably equal to or greater than the total volume of all the thread segments 8 and 10.

It is believed that the configuration of the tapping grooves can have a marked effect on the tendency of the cup shell 2 to jam during insertion. Wide tapping grooves may have a tendency to allow large irregularities in the bone to enter the groove causing the implant to jam with the risk of bone fracture if high forces are applied. The presence of numerous narrow tapping grooves equally spaced could cause similar problems due to the relatively short length of the thread segments. Accordingly, the tapping grooves 16 are arranged in pairs by dividing the thread into alternating longer and shorter segments 8 and 10. The longer thread segments 8 are preferably at least 50% longer than the short segments 10, and usually not more than 1800%. Most preferably the long thread segments 8 are 500% longer than the short segments 10.

The configuration of thread segments 8 and 10 described above extends over the fully formed portion of the thread. The lead-in and lead-out portion of thread do not necessarily conform to this configuration. In particular, in the case of a hemispherical cup shell 2 the lead end of the thread may start in the region of the pole of the hemisphere and the above configuration is not applicable since the thread radius increases in the lead portion.

As various changes could be made in the above constructions without departing from the scope of the invention, it is intended that all matter contained in the above description or shown in the drawings shall be interpreted as illustrative and not in a limiting sense.

I claim:

1. An acetabular implant of a hip joint prosthesis comprising a generally hemispherical or frustoconical metal cup shell having an external self-tapping thread extending around the circumference of the shell, the thread being divided by a plurality of tapping grooves into a plurality of thread segments having leading and trailing ends, the thread segments having radii continuously-progressively decreasing from the leading end toward the trailing end of each segment.

2. An acetabular implant according to claim 1 wherein the thread depth of each thread segment decreases from the leading to the trailing end of the segment by at least 3 percent and not more than 30 percent.

3. An acetabular implant according to claim 2 wherein the thread depth of each thread segment decreases from the leading to the trailing end of the segment by approximately 10 percent.

4. An acetabular implant according to claim 2 wherein each thread segment has a width progressively decreasing from the leading end toward the trailing end of the segment.

5. An acetabular implant of a hip joint prosthesis comprising a generally hemispherical or frustoconical metal cup shell having an external self-tapping thread extending around the circumference of the shell, the thread being divided by a plurality of tapping grooves into a plurality of thread segments having leading and trailing ends, the thread segments having radii progressively decreasing from the leading end toward the trailing end of each segment, each thread segment having a thread depth decreasing from the leading to the trailing end of the segment by at least 3 percent and not more than 30 percent, and the tapping grooves being arranged in pairs dividing the thread segments into alternating long and short thread segments.

6. An acetabular implant according to claim 5 wherein the thread tapping grooves have a total volume at least equal to the total volume of all of the thread segments.

7. An acetabular implant according to claim 6 wherein the long thread segments are 50–1800 percent longer than the short thread segments.

8. An acetabular implant according to claim 7 wherein the long thread segments are approximately 500 percent longer than the short thread segments.

9. An acetabular implant of a hip joint prosthesis comprising a generally hemispherical or frustoconical metal cup shell having an external self-tapping thread extending around the circumference of the shell, the thread being divided by a plurality of tapping grooves into a plurality of thread segments having leading and trailing ends, the thread segments having radii progressively decreasing from the leading end toward the trailing end of each segment, and the tapping grooves being arranged in pairs dividing the thread segments into alternating long and short thread segments.

10. An acetabular implant according to claim 9 wherein each thread segment has a width progressively decreasing from the leading end toward the trailing end of the segment.

11. An acetabular implant according to claim 9 wherein the thread tapping grooves have a total volume at least equal to the total volume of all of the thread segments.

12. An acetabular implant of a hip joint prosthesis comprising a generally hemispherical or frustoconical metal cup shell having an external self-tapping thread extending around the circumference of the shell, the thread being divided by a plurality of tapping grooves into a plurality of thread segments having leading and trailing ends, the thread segments having radii progressively decreasing from the leading end toward the trailing end of each segment, each thread segment having a width progressively decreasing from the leading end toward the trailing end of the segment, and the tapping grooves being arranged in pairs dividing the thread segments into alternating long and short thread segments.

13. An acetabular implant according to claim 12 wherein the long thread segments are 50–1800 percent longer than the short thread segments.

14. An acetabular implant according to claim 13 wherein the long thread segment are approximately 500 percent longer than the short thread segments.

15. An acetabular implant according to claim 14 wherein the long thread segments are 50–1800 percent longer than the short thread segments.

16. An acetabular implant according to claim 15 wherein the long thread segments are approximately 500 percent longer than the short thread segments.

* * * * *

UNITED STATES PATENT AND TRADEMARK OFFICE
CERTIFICATE OF CORRECTION

PATENT NO. : 4,997,447
DATED : March 5, 1991
INVENTOR(S) : Philip Shelley It is certified that error appears in the above-identified patent and that said Letters Patent is hereby corrected as shown below: Title page:

Item (30): "Foreign Application Priority Data" should have been shown to reflect priority from British Patent Appln. No. 88.19588.8, filed August 17, 1988.

Col. 2, line 22, after "depth" insert --,--.
Col. 4, line 3, "6" should read --5--.
Col. 4, line 46, "segment" should read --segments--.
Col. 4, line 48, "14" should read --9--.

Signed and Sealed this

Seventeenth Day of August, 1993

*Attest:*

BRUCE LEHMAN

*Attesting Officer*    *Commissioner of Patents and Trademarks*